United States Patent [19]

Aubigne et al.

[11] Patent Number: 5,416,237
[45] Date of Patent: May 16, 1995

[54] PROCESS FOR THE PRODUCTION OF ACETIC ACID

[75] Inventors: Simon D. Aubigne, Carry-le-Rouet, France; Jeremy B. Cooper, West Sussex, England; Bruce L. Williams, North Humberside, England; Derrick J. Watson, East Yorkshire, England

[73] Assignee: BP Chemicals Limited, London, England

[21] Appl. No.: 276,873

[22] Filed: Jul. 18, 1994

Related U.S. Application Data

[63] Continuation of Ser. No. 66,724, May 24, 1993, abandoned.

[30] Foreign Application Priority Data

Jun. 2, 1992 [GB] United Kingdom ............... 9211671

[51] Int. Cl.$^6$ .................. C07C 51/44; C07C 51/12
[52] U.S. Cl. .................. 562/519; 562/517; 562/520; 562/406; 562/607; 562/608
[58] Field of Search ............ 562/519, 517, 520, 406, 562/607, 608

[56] References Cited

U.S. PATENT DOCUMENTS

| | | |
|---|---|---|
| 3,769,329 | 10/1973 | Paulik et al. |
| 3,845,121 | 10/1974 | Eubanks et al. ............... 562/517 X |
| 3,855,307 | 12/1974 | Rony et al. ............... 562/517 X |
| 4,007,130 | 2/1977 | Leach et al. |
| 4,374,070 | 2/1983 | Lartin et al. |
| 4,628,041 | 12/1986 | Smith et al. |
| 4,994,608 | 2/1991 | Torrence et al. |
| 5,001,259 | 3/1991 | Smith et al. |
| 5,026,908 | 6/1991 | Smith et al. |
| 5,144,068 | 9/1992 | Smith et al. |
| 5,237,097 | 8/1993 | Smith et al. ............... 562/517 X |

FOREIGN PATENT DOCUMENTS

| | | |
|---|---|---|
| 0055618 | 7/1982 | European Pat. Off. |
| 0144935 | 6/1985 | European Pat. Off. |
| 0144936 | 6/1985 | European Pat. Off. |
| 0153834 | 9/1985 | European Pat. Off. |
| 0161874 | 11/1985 | European Pat. Off. |
| 0196173 | 10/1986 | European Pat. Off. |
| 0250189 | 12/1987 | European Pat. Off. |
| 0265140 | 4/1988 | European Pat. Off. |
| 0296584 | 12/1988 | European Pat. Off. |
| 0361785 | 4/1990 | European Pat. Off. |
| 0384652 | 8/1990 | European Pat. Off. |
| 0391680 | 10/1990 | European Pat. Off. |
| 0482787 | 4/1992 | European Pat. Off. |
| 0484020 | 5/1992 | European Pat. Off. |
| 0506240 | 9/1992 | European Pat. Off. |
| 0538040 | 10/1992 | European Pat. Off. |
| 959183 | 2/1957 | Germany. |
| 50-083315A | 7/1977 | Japan. |
| 54-1153113A | 9/1979 | Japan. |
| 1233121 | 5/1971 | United Kingdom. |
| 1343855 | 1/1974 | United Kingdom. |
| 1350726 | 4/1974 | United Kingdom. |
| 2112394 | 7/1983 | United Kingdom. |
| 2146637 | 4/1985 | United Kingdom. |

OTHER PUBLICATIONS

Eby, R. T. & Singleton, T. C., Applied Industrial Catalysis, vol. 1, pp. 275–296 (1983).

*Primary Examiner*—Arthur C. Prescott
*Attorney, Agent, or Firm*—Brooks Haidt Haffner & Delahunty

[57] ABSTRACT

In a process for the production of acetic acid by carbonylation of methanol in the presence of a rhodium carbonylation catalyst, methyl iodide and an iodide salt stabiliser the improvement resides in maintaining a finite concentration of water of up to about 10% by weight and a methyl acetate concentration of at least 2% by weight in the liquid reaction composition and recovering the acetic acid product by passing the liquid reaction composition through a flash zone to produce a vapour fraction which is passed to a single distillation column from which an acetic acid product is removed.

27 Claims, No Drawings

PROCESS FOR THE PRODUCTION OF ACETIC ACID

This application is a continuation of application Ser. No. 08/066,724, filed May 24, 1993 now abandoned.

This invention relates to a process for the production of acetic acid and in particular to a process for the production of acetic acid by carbonylation of methanol.

Processes for the production of acetic acid by carbonylation of methanol are well known and are operated industrially.

Thus, UK patent GB 1,233,121 describes a process for the production of an organic acid or its corresponding ester by carbonylation using a rhodium catalyst.

When it is desired to obtain pure carboxylic acid from such processes it is necessary to remove contaminants such as water, iodide compounds and higher boiling contaminants such as propionic acid as in the case of carbonylation processes for the production of acetic acid.

UK patent GB 1,350,726 describes a process for the purification of monocarboxylic acid streams containing water and alkyl halide and/or hydrogen iodide contaminants, which process comprises (a) introducing a monocarboxylic acid stream containing water and alkyl halide and/or hydrogen halide contaminants into the upper half of a distillation zone, (b) removing an overhead fraction containing a major proportion of the water and any alkyl halide charged to the zone, (c) removing a stream from the middle portion of the zone and below the point of introduction in (a) containing a major proportion of any hydrogen halide present in the zone, and (d) removing a product monocarboxylic acid stream from the lower part of the zone, the product acid stream being substantially dry and substantially free of any alkyl halide or hydrogen halide contaminants charged to the zone. Although in the examples a product acid stream containing 87 to 132 ppm water was obtained from a process stream containing from 17.86 to 19.16 percent by weight water in a single, 40-plate distillation column, it is our belief that such a system would require significantly large column feed and overhead process stream flow rates and therefore large energy and column diameter requirements.

UK patent GB 1,343,855 describes a similar system for the purification of carboxylic acids but uses two separation stages.

In a process for the production of acetic acid by carbonylation of methanol, described by R. T. Eby and T. C. Singleton in Applied Industrial Catalysis, Vol 1, p275-296, 1983, crude acetic acid product is purified in three separate distillation stages (a) a light ends column in which a heads light ends stream and a base heavy ends stream are separated for recycle to the reactor from a wet acetic acid side stream, (b) a drying stage in which the wet acetic acid is dried by distillation, the separated water being recycled to the reactor, and (c) a heavy ends column in which propionic acid by-product is separated from the dry acetic acid. In such a process the water concentration in the carbonylation reaction medium is relatively high, for example up to about 14–15 weight percent and removal of this water represents a significant cost to the process for producing pure, dry acetic acid.

European published patent application number EP-A-0161874 describes a reaction system by means of which an alcohol, as exemplified by methanol, can be carbonylated to a carboxylic acid derivative such as acetic acid while using a liquid reaction medium having a low water content. This is achieved by the use of defined concentrations of an iodide salt, alkyl iodide and ester in the liquid reaction medium to maintain rhodium catalyst stability and reactor productivity. EP-A-0161874 recognises that water is an undesirable component of the crude acetic acid and that the more water there is in the stream the greater will be the operating costs and required capital investment in the product recovery-purification system. However, in example 1 of EP-A-016187, although the water concentration of the liquid reaction medium is reduced to 4 to 5 weight percent from a prior art value of approximately 15 weight percent, the water concentration of the crude acetic acid from the methyl iodide-acetic acid splitter column is only reduced to approximately 4 to 7 weight percent and would therefore require further purification to remove the remaining water. According to European patent application number EP-A-0265140 which describes the same process as in EP-A-0161874, one such method of drying the acid is a drying column.

We have now found that by operating a liquid-phase carbonylation reaction with a defined liquid reaction medium composition it is possible to use an improved product recovery system which uses a single distillation zone.

Thus according to the present invention there is provided a process for the production of acetic acid which process comprises:
(a) feeding methanol and carbon monoxide to a carbonylation zone in which there is maintained during the course of the process a liquid reaction composition comprising:
 (i) a rhodium carbonylation catalyst;
 (ii) methyl iodide;
 (iii) a carbonylation catalyst stabiliser comprising an iodide salt which is soluble in the reaction composition;
 (iv) a finite amount of water at a concentration of up to about 10% by weight preferably up to about 8% by weight;
 (v) methyl acetate at a concentration of at least 2% by weight; and
 (vi) acetic acid,
(b) withdrawing liquid reaction composition from the reactor and introducing it, with or without the addition of heat, to a flash zone to form a vapour fraction comprising water up to about 8% by weight preferably up to about 6% by weight, acetic acid product, propionic acid by-product and the majority of the methyl acetate and methyl iodide from the flash zone feed, and a liquid fraction comprising involatile rhodium catalyst, involatile catalyst stabiliser, acetic acid, water and the remainder of the methyl acetate, methyl iodide and propionic acid by-product from the flash zone feed,
(c) recycling the liquid fraction from the flash zone to the reaction zone, and recovering acetic acid product from the flash zone vapour fraction by use of a single distillation zone by:
(d) introducing the vapour fraction (as a vapour and/or liquid) from the flash zone into the distillation zone,
(e) removing from the head of the distillation zone a light ends recycle stream comprising water, methyl acetate, methyl iodide and acetic acid, and (f) removing from the distillation zone at a point below the introduction point of the flash zone vapour fraction, an acid product stream comprising acetic acid having a water concentration of less than 1500 ppm, preferably less than 500 ppm and a propionic acid concentration of less than 500 ppm, preferably less than 200 ppm.

In the present invention the use of a defined reaction liquid reaction composition and limited water concentration in the flash zone vapour fraction allows the product acetic acid to be purified by use of a single distillation zone.

The process of the present invention may be performed as a batch or continuous process, preferably as a continuous process. The methanol feed to the carbonylation zone may be essentially pure as prepared by known industrial processes.

The carbon monoxide fed to the reactor may be essentially pure or may contain inert impurities such as carbon dioxide, methane, nitrogen, noble gases, water and $C_1$ to $C_4$ paraffinic hydrocarbons such as are known in the art. The partial pressure of carbon monoxide in the reactor is suitably maintained at 2.5 to 100 bara, preferably at 3 to 20 bara. Hydrogen present in the reactor as a result of the water gas shift reaction and optionally as part of the gas feed is preferably maintained at a partial pressure of at least 2 psi, preferably up to a maximum partial pressure of about 150 psi.

The carbonylation zone is preferably maintained at a pressure in the range 17 to 100 bara, preferably in the range 20 to 40 bara.

The carbonylation zone is preferably maintained at a temperature in the range 150° to 250° C., most preferably in the range 170° to 220° C.

The rhodium carbonylation catalyst concentration in the liquid reaction composition is preferably maintained at a concentration in the range 100 to 2500 ppm rhodium, most preferably in the range 150 to 1000 ppm. The rhodium carbonylation catalyst may be introduced to the carbonylation zone in any suitable form known in the art.

The carbonylation catalyst stabiliser is preferably an iodide salt of an alkali or alkaline earth metal or is a quarternary ammonium iodide or a quaternary phosphonium iodide. The alkali metals are lithium, sodium, potassium, rubidium and cesium. The alkaline earth metals are beryllium, magnesium, calcium, strontium, barium and radium. Preferably, the catalyst stabiliser is an iodide salt of lithium, sodium, potassium or calcium, most preferably an iodide salt of lithium. The catalyst stabiliser may also be a quarternary ammonium iodide salt such a quarternised amine, pyridine, pyrrolidine or imidazole, e.g. N,N' dimethyl imidazolium iodide or other heterocyclic nitrogen containing compound. Suitable heterocyclic iodide catalyst stabilisers are described in EP-A-0391680 which describes the use of catalyst stabilisers selected from the group consisting of quarternary ammonium iodides having the formula:

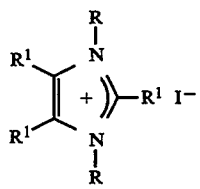
(1)

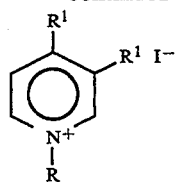
(2)

and

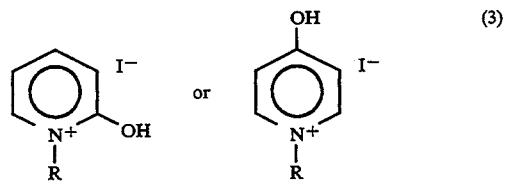
(3)

wherein the R and $R^1$ groups are independently selected from hydrogen or $C_1$ to $C_{20}$ alkyl groups with the proviso that at least one $R^1$ group is other than hydrogen.

According to EP-A-0391680 it is preferred that at least one of the R groups is the same as the $R^2$ group comprising the organic moiety of the alcohol, iodide derivative and carboxylic acid. The $R^1$ groups on the other hand are suitably hydrogen or $C_1$ to $C_8$ alkyl, preferably hydrogen or $C_1$ to $C_6$ alkyl with the proviso defined above. Examples of preferred catalyst stabilisers in each of classes (1) and (2) are those where the $R^1$ groups are selected from hydrogen, methyl, ethyl, n-propyl, iso-propyl, n-butyl, sec-butyl and t-butyl.

One particularly preferred class of catalyst stabilisers are iodide salts of the cation:

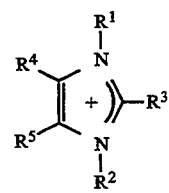

where
(i) $R^1$ and $R^2$ are methyl
(ii) $R^5$ is hydrogen
(iii) $R^3$ is $C_1$ to $C_{20}$ alkyl or hydrogen, and
(iv) $R^4$ is $C_1$ to $C_{20}$ alkyl Most preferred examples of this class are where (1) $R^3=C_2H_5$, $R^1$, $R^2$ and $R^4=CH_3$ and $R^5=H$ or (2) $R^3$ and $R^5=H$ and $R^1$, $R^2$ and $R^4=CH_3$.

Another particularly important class of catalyst stabiliser is comprised of iodide salts of the cation

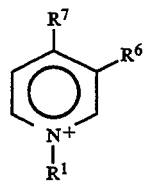

where $R^6$ is either hydrogen or methyl, $R^7$ is $C_1$ to $C_4$ alkyl and $R^1$ is methyl. Preferred examples are where (1) $R^6=H$ and $R^7=C_2H_5$, (2) $R^6=H$ and $R^7=t-C_4H_9$ and (3) $R^6$ and $R^7=CH_3$.

Suitable quaternary phosphinium iodides include methyl tributyl phosphonium iodide, tetrabutyl phosphonium iodide, methyl triphenyl phosphonium iodide and the like.

The iodide catalyst stabiliser may be introduced directly to the carbonylation reactor. Alternatively, the iodide salt may be generated in-situ since under the operating conditions of the carbonylation reactor a wide range of precursors will react with methyl iodide to generate the iodide stabiliser. Metal iodide stabilisers may be generated from $C_1$ to $C_6$ carboxylate salts, e.g. acetate or propionate salts and quarternary iodides may be generated from the corresponding amine or phosphine.

The concentration of carbonylation catalyst stabiliser in the liquid reaction composition should be sufficient to maintain at a suitable level, the activity and stability of the rhodium carbonylation catalyst at the water concentrations in the liquid reaction composition. Preferably the catalyst stabiliser is present at a concentration of at least 0.4 mol per liter of liquid reaction medium measured at cold degassed conditions and up to the solubility limit of the stabiliser, most preferably 0.8 mol/l to 1.8 mol/l.

It has been found that certain selected iodide salts suppress the volatility of water relative to that of acetic acid and so their presence in the liquid reaction composition reduces the concentration of water relative to acetic acid in the vapour fraction produced when the liquid reaction composition is introduced into the flash zone. These iodide salts are iodides of alkali or alkaline earth metals or of hydrogen or aluminium, preferably iodides of lithium, sodium or potassium. Such iodide salts may be present in addition to iodide catalyst stabilisers or where the relative volatility suppressing iodide salt can also act as a catalyst stabiliser such a salt may be present for both functions of relative volatility suppression and carbonylation catalyst stabilisation. The presence of these relative volatility suppression iodide salts can allow the concentration of water in the flash zone vapour fraction to be controlled to the level necessary to achieve acetic acid product purification with a single distillation column in situations where in the absence of the relative volatility suppressant the water concentration in the liquid reactor composition would produce an unacceptably high water concentration in the flash zone vapour fraction. Thus, in the absence of such water relative volatility suppressants the water concentration in the liquid reaction composition should be maintained at no more than about 8% by weight in order that a water concentration of up to 8% can be achieved in the vapour fraction from the flash zone or no more than about 6% by weight if a water concentration of up to 6% is to be achieved in the flash zone vapour fraction. With an effective amount of water relative volatility suppressant the water concentration in the liquid reaction composition may be increased up to 10% by weight to achieve up to about 8% by weight water in the flash zone vapour fraction or up to about 8% by weight to achieve up to about 6% by weight water in the flash zone vapour fraction. The use of such iodide salts is described in our European Patent Application Publication number EP0506240, Application No. 92301825.3. Suitable concentrations of relative volatility suppressing iodide salts are in the range 0.1% to 50% by weight subject to the limit of solubility of the salt. It will be appreciated that the relative volatility suppression effect may be as a result of a reduction in the volatility of the water or an increase in the volatility of the acetic acid or a combination of both effects.

The methyl acetate concentration in the liquid reaction composition is preferably in the range 2% to 15% by weight, preferably in the range 3% to 10% by weight. As the methyl acetate concentration in the liquid reaction composition is increased, the amount of propionic by-product decreases. By operating with at least 2% methyl acetate the concentration of propionic acid by-product in the liquid reaction composition is sufficiently low that its concentration in the acid product is below that level at which further purification is required, that is less than about 500 ppm.

The water concentration in the reactor is up to about 10% by weight preferably up to about 8% by weight, preferably up to 6% by weight, most preferably about 1 to 5% by weight.

Metal-iodides may be present in the liquid reaction composition as a result of corrosion of the reaction zone and associated equipment as well as being recycled to the reaction zone with returned process streams. Corrosion metals may comprise one or more of iron, chromium, manganese, nickel, molybdenum and the like. According to EP-A-0384652, chromium and molybdenum may be beneficial to the carbonylation reaction. However, as the concentration of corrosion metals such as iron and nickel is increased, the concentration of by-product propionic acid in the liquid reaction composition increases. Therefore, whilst the total amount of corrosion metals should be maintained at a low level, it is preferable to selectively maintain particular corrosion metals such as iron, manganese and nickel at the lowest values possible. The concentration of corrosion metals which have an adverse effect on the process should be maintained as low as possible, for example typically less than 1000 ppm, preferably less than 500 ppm, most preferably less than 200 ppm in total. The adverse effect of iron and nickel in increasing by-product propionic acid production may be off-set to some extent by increasing the methyl acetate concentration. Methods for removing metal iodides from carbonylation catalysts are known in the art, for example methods which might be used are described in U.S. Pat. No. 4,007,130; U.S. Pat. No. 4,628,041 and EP-A-0265140.

Acetic acid may comprise the balance of the liquid reaction composition together with other minor components including by-product propionic acid.

The flash zone is preferably maintained at a pressure below that of the reaction zone typically at a pressure of 1 to 6 bara. The flash zone is preferably maintained at a temperature of 100 to 160° C.

The vapour fraction may be introduced to the distillation zone as a vapour or the condensible components therein may be partially or fully condensed and the vapour fraction may be introduced as a mixed vapour/liquid or as a liquid with non-condensibles.

The distillation zone preferably has up to 25 theoretical stages. Since distillation zones may have differing efficiencies this may be equivalent to 35 actual stage with an efficiency of about 0.7 or 50 actual stages with an efficiency of about 0.5. Most preferably the distillation zone has up to about 18 theoretical stages. Preferably, the distillation zone has about 4 to 15 theoretical rectifying stages above the feed point. Preferably, the distillation zone has up to about 14 theoretical stripping stages below the feed point and above the base of the zone, most preferably about 3 to 14 theoretical stages. A suitable distillation zone, may have 18 theoretical stages with feed at theoretical stage 3 to 8 from the base and a crude acetic acid product take off as a liquid from the base of the zone. Another suitable distillation zone may have 20 theoretical stages with feed at theorectical stage 8 to 15 from the base and a crude acetic acid product take-off as a liquid from the base of the zone.

Preferably, the product acid stream may be removed at the base of the distillation zone or at a point 2 actual stages above the base of the distillation zone. The acid product may be withdrawn as a liquid or a vapour. When the acid product is withdrawn as a vapour preferably a small liquid bleed is also taken from the base of the zone.

Suitably the distillation zone may be operated at a heads pressure of about 1.3 bare and a base pressure of about 1.4 bare but higher or lower pressures may be used. The operating temperatures of the distillation zone will depend upon the composition of the feed, heads and base streams and the operating pressure. Typical base temperatures are 147° to 149° C. and heads temperatures are 115° to 118° C. The distillation zone may be operated with suitable return of reflux to the head of the distillation zone, for example at a rate of 1.5 times the heads product take-off rate.

It is expected that hydrogen iodide may be present in the feed to the distillation zone. The build up of this component may be prevented by introducing a small feed of methanol to the distillation zone, preferably below the feed point, to convert the hydrogen iodide to methyl iodide which is removed in the light ends recycle stream. It is expected that up to 5000 ppm hydrogen iodide in the feed may be treated in this way. Alternatively, or in addition, by operating the distillation zone at sufficiently elevated pressure, the operating temperatures in the distillation zone may be sufficient for the relatively high concentration of methyl acetate in the distillation zone to convert the hydrogen iodide to methyl iodide which is removed in the light ends recycle stream.

It will often be the case that the vapour stream passing overhead from the distillation zone will be two phase when it is cooled. When the overhead stream is two phase it is preferred that reflux to the distillation zone be provided by separating the phases and using only the light, aqueous phase; the heavy, methyl iodide-rich phase being recycled to the reactor with the remaining light, aqueous phase as light ends recycle. The light ends recycle may comprise less than 5% by weight acetic acid.

Iodide impurities in the acetic acid product from the single distillation zone may conveniently be removed by passing the acid through one or more ion exchange resin beds. Alternatively, the iodide impurities may be removed by use of a silver salt scavanger as described in EP 0361785.

The acetic acid product may be purified to remove anionic iodide contaminants by passing it through an anion exchange resin bed such as described in UK patent application GB 2,112,394 the contents of which are hereby incorporated by reference. A particularly preferred resin for removing anionic iodide is a macroreticular weak base resin such as Reillex 425 (trade mark) which is a macrorecticular poly 4-vinylpyridine weak base resin having high temperature stability. Also preferred is the weakly basic resin Lewatit MP62 (trade mark), which is a macroporous anion exchange resin with tertiary amine groups (mono functional).

The acetic acid may be purified to remove organic iodide contaminants by passing it through a silver-loaded resin bed such as described in our European patent application publication EP0482787; application number 91309235.9 which describes a process for removing iodide compounds from a carboxylic acid using an ion exchange resin having functional groups which each have at least one sulphur-donor atom and which resin has at least 1% of its sulphur-donor functional groups occupied by silver, palladium and/or mercury. Preferably the resin has thiol or substituted thiol groups. Preferred thiol groups comprise —SH groups, aliphatic thiol groups, aryl thiol groups, alicyclic thiol groups and/or thiouronium groups and preferred substituted thiol groups comprise isothiouronium groups.

Other suitable resins for removing organic iodides are described in EP-A-0296584 which describes a method of producing silver-exchanged macroreticular resins suitable for removing halides from liquid carboxylic acid contaminated with a halide impurity.

Suitable resins are also described in European patent application number EP-A-0196173 which describes a method for removing iodide compounds from a non-aqueous organic medium by contacting with a macroreticular strong acid cation exchange resin which has at least 1% of its active sites in the silver or mercury form.

Yet another class of resins suitable for removing iodide derivatives are described in our European patent application publication EP 0484020, application number EP 91309650.9 which describes a process for removing iodide derivatives from liquid acetic acid using a strong acid cation exchange resin having from about 4% to about 12% crosslinking, a surface area in the proton exchanged form of less than $10m^2g^{-1}$ after drying from the water wet state and a surface area of greater than $10m^2g^{-1}$ after drying from a wet state in which water has been replaced by methanol, said resin having at least 1% of its active sites converted to the silver form. Preferred resins are Purolite C145, Purolite CT145, Bayer K2441, Bayer K2431 and Bayer K2411 (trade marks) which have at least 1% of their active sites in the silver form.

Preferably the acetic acid is passed through one or more resin beds to remove anionic iodide contaminants before being passed through a resin bed to remove organic iodide contaminants thereby increasing the operating life of the organic iodide-removal resin beds which would be rapidly saturated by anionic iodide contaminants which are generally present in greater quantities than organic iodides.

The operating lives of the silver-loaded resins are preferably extended by the use of strong acid cation exchange resin in the proton form to remove metal ion contaminants as described in our European patent application publication EP 0538040, application number EP 92309425.4.

The level to which the iodide concentrations are reduced will depend upon the intended use of the acetic acid product. Iodide contaminants may typically be reduced to less than several hundred ppb and preferably to less than 10 ppb.

The invention will now be illustrated by reference to the following examples.

Methanol was continuously carbonylated in the presence of a rhodium carbonylation catalyst, methyl iodide, lithium iodide catalyst stabiliser, a finite water concentration of up to about 10% by weight, methyl acetate at a concentration of at least 2% by weight and acetic acid, in a 6 liter zirconium, stirred reactor with a working mass of 4 kg (measured at ambient temperature in a bubble free state) at a pressure of 30 barg and a temperature in the range 180°–190° C. The temperature in the reactor was maintained by a hot oil jacket. Carbon monoxide was fed to the reactor on pressure demand via a sparge below the stirrer. Liquid reaction composition was continuously withdrawn from the reactor and passed to a flash tank operated at a pressure of 1.4 barg and a temperature of about 130° C. A vapour fraction comprising acetic acid product, propionic acid by-product, methyl iodide, methyl acetate and up to about 8% by weight water was passed overhead from the flash tank through an irrigated packed section and through a demister. The vapour fraction was condensed and introduced as a liquid into a distillation column operated at 1.2–1.3 barg. The liquid fraction from the flash tank comprising involatile rhodium catalyst, involatile lithium salt stabiliser, acetic acid, water and the remainder of the methyl iodide, methyl acetate and propionic acid was recycled to the reactor.

In the distillation column the acetic acid product was removed from the base. The methyl iodide, methyl acetate and water, together with some of the acetic acid passed overhead and were condensed into two phases. The light, aqueous phase was split: some was used as reflux to the column, the remainder was recycled to the reactor together with the heavy, methyl iodide rich phase as light ends recycle. Methanol could be fed into the column to react with any hydrogen iodide present; the methyl iodide and water produced being removed overhead.

The non-condensibles from the flash tank vapour and the head of the distillation column were first cooled to minimise the loss of volatiles from the process. The resulting off-gas stream was then passed to a scrubber where it was contacted countercurrently with chilled methanol. The methanol leaving the base of the scrubber was added to pure methanol and used as feed to the reactor.

The carbonylation and distillation stages of the process of the present invention were illustrated by the following two examples using the general procedure outlined above.

EXAMPLE 1

1.25 kgh$^{-1}$ methanol and 1.36 kgh$^{-1}$ carbon monoxide were fed continuously into the reactor held at an average of 186.6° C. The average composition of the reactor contents was: 2.6 wt % methyl acetate, 5.6 wt % water, 14.0 wt % methyl iodide, 61.9 wt % acetic acid, 0.55 wt % lithium (present at least in part as iodide salt) and 11.6 wt % iodide with 580 ppm rhodium, 190 ppm iron and 50 ppm chromium. The lithium iodide in the reactor composition functioned both as a carbonylation catalyst stabiliser in the reactor and a water relative volatility suppressant in the flash tank.

A feed to the distillation column of about 4.3 l h$^{-1}$ containing 3.8 wt % water, 43.3 wt % methyl iodide, 5.3 wt % methyl acetate and 48.8 wt % acetic acid was obtained. The distillation column in this example contained 35 PTFE sieve trays (stages) with the feed point at tray 20 (numbering from the bottom) with methanol fed at tray 8. A reflux ratio of 1.5 on a volume basis was employed. An acetic acid product stream of 2.26 kgh$^{-1}$ was obtained from the base of the column which contained 460 ppm water, 180 ppm propionic acid and 1.7 ppm iodide.

The light ends recycle stream from the head of the distillation column was recycled to the reactor as two streams; methyl iodide rich stream containing <1 wt % water, <1 wt % acetic acid and 12.9 wt % methyl acetate and an aqueous stream containing 1.3 wt % methyl iodide, 8.8 wt % methyl acetate and <1 wt % acetic acid. Light, aqueous phase from the cooled column overhead vapour was fed to the column as reflux at a rate of 3.4 lh$^{-1}$.

EXAMPLE 2

1.26 kgh$^{-1}$ methanol and 1.34 kgh$^{-1}$ carbon monoxide were fed continuously into the reactor held at an average of 183.6° C. The average composition of the reactor contents was: 5.6 wt % methyl acetate, 4.4 wt % water, 14.7 wt % methyl iodide, 55.0 wt % acetic acid, 1.18 wt % lithium (present at least in part as iodide salt and functioning as carbonylation catalyst stabiliser and relative volatility suppressant) and 15.7 wt % iodide with 425 ppm rhodium, 60 ppm iron and 15 ppm chromium.

A feed to the distillation column of about 4.7 lh$^{-1}$ containing 2.4 wt % water, 36.0 wt % methyl iodide, 16.7 wt % methyl acetate and 43.9 wt % acetic acid was obtained. The distillation column was configured as described for Example 1. An acetic acid product stream of 2.31 kgh$^{-1}$ was obtained from the base of the column which contained 303 ppm water, 130 ppm propionic acid and 0.38 ppm iodide.

The light ends recycle was again recycled to the reactor as two streams. The methyl iodide rich stream contained <1 wt % water, <1 wt % acetic acid and 22.4 wt % methyl acetate. The aqueous stream contained 2.3 wt % methyl iodide, 9.6 wt % methyl acetate and 1.9 wt % acetic acid. Light, aqueous phase reflux was fed to the column at a rate of 3.3 l h$^{-1}$.

It is expected that the acetic acid products from Examples 1 and 2 may be purified of iodide contaminants by passing through suitable ion exchange resin beds. In this way pure acetic acid may be obtained using a single distillation zone without excessive recycle of acetic acid overhead.

EXAMPLES 3 to 5

Further examples using the general procedure outlined above for Examples 1 and 2 were performed using the reaction conditions given in Table 1 below:

TABLE 1

| | REACTOR CONDITIONS | | |
|---|---|---|---|
| Example | 3 | 4 | 5 |
| Feeds | | | |
| Methanol (kg/hr)* | 1.26 | 1.23 | 1.24 |
| Carbon Monoxide (kg/hr) | 1.26 | 1.18 | 1.14 |
| Reactor | | | |
| Temperature (°C.) | 188.5 | 189.1 | 186.9 |
| Pressure (barg) | 30 | 30 | 26 |
| Liquid Reactor Composition | | | |
| Methyl Acetate (%) | 2.9 | 3.1 | 7.3 |
| Water (%) | 2.0 | 1.9 | 4.2 |
| Methyl Iodide (%) | 15.2 | 12.0 | 13.9 |
| Acetic Acid (%) | 63.3 | 67.4 | 53.4 |
| Lithium (%) | 0.76 | 0.63 | 0.88 |
| Iodide (%) | 12.0 | 13.8 | 15.1 |
| Rhodium (ppm) | 550 | 550 | 320 |
| Iron (ppm) | 290 | 270 | 80 |
| Chromium (ppm) | 70 | 80 | 60 |

*Including methanol fed to the distillation column.

The distillation column conditions are given in Table 2 below:

TABLE 2

DISTILLATION COLUMN CONDITIONS

| Example | 3 | 4 | 5 |
|---|---|---|---|
| Number of Actual Trays | 26 | 26 | 28 |
| Feed at Tray* | 7 | 15 | 20 |
| Methanol Feed | | | |
| Tray | 6 | 6 | 8 |
| Rate (g/hr) | 55 | 55 | 50 |
| Feed (l/hr) | 3.7 | 4.0 | 5.1 |
| Feed Composition (%) | | | |
| Methyl Acetate | 6.2 | 8.8 | 15.7 |
| Water | 1.0 | 1.9 | 2.6 |
| Methyl Iodide | 43.8 | 47.7 | 39.7 |
| Acetic Acid | 51.7 | 45.6 | 39.0 |
| Reflux (l/hr) | 2.3 | 3.4 | 4.6 |

*Numbered from the base.

The compositions and flow rates of the process streams from the distillation column are given in Table 3 below:

TABLE 3

DISTILLATION COLUMN PROCESS STREAMS

| Example | 3 | 4 | 5 |
|---|---|---|---|
| Overhead Methyl Iodide Rich Stream | | | |
| Water (%) | 0.6 | 0.6 | 1.3 |
| Acetic Acid (%) | 0.4 | 0.7 | 1.1 |
| Methyl Acetate (%) | 13.8 | 14.5 | 26.2 |
| Overhead Water Rich Stream | | | |
| Methyl Iodide (%) | 1.4 | 1.5 | 1.7 |
| Methyl Acetate (%) | 7.0 | 8.3 | 11.2 |
| Acetic Acid (%) | 4.2 | 7.0 | 5.8 |
| Acid Product | | | |
| Rate (kg/hr) | 2.33 | 2.19 | 2.33 |
| Water (ppm) | 470 | 670 | 320 |
| Propionic Acid (ppm) | 120 | 100 | 64 |
| Iodide (ppm) | 0.7 | 0.4 | 0.3 |

The acetic acid product from the distillation column in Example 5 was passed through a bed of Lewatit MP-62 resin at 80° C. at a rate of 10 resin bed volumes of acetic acid treated per hour to remove anionic iodide contaminants to less than 1 ppb. The combined overhead streams forming the light ends recycle stream were calculated to have 0.96% by weight acetic acid and 1.33% by weight acetic acid in Examples 4 and 5 respectively, that is less than 5% by weight acetic acid.

We claim:

1. A process for the production of acetic acid which process comprises:
   (a) feeding methanol and carbon monoxide to a carbonylation zone in which there is maintained during the course of the process a liquid reaction composition comprising:
   (i) a rhodium carbonylation catalyst;
   (ii) methyl iodide;
   (iii) a carbonylation catalyst stabiliser comprising an iodide salt which is soluble in the reaction composition;
   (iv) a finite amount of water at a concentration of up to about 10% by weight;
   (v) methyl acetate at a concentration of at least 2% by weight; and
   (vi) acetic acid,
   (b) withdrawing liquid reaction composition from the reactor and introducing it, with or without the addition of heat, to a flash zone to form a vapour fraction comprising water up to about 8% by weight, acetic acid product, propionic acid by-product and the majority of the methyl acetate and methyl iodide from the flash zone feed, and a liquid fraction comprising involatile rhodium catalyst, involatile catalyst stabiliser, acetic acid, water and the remainder of the methyl acetate, methyl iodide and propionic acid by-product from the flash zone feed,
   (c) recycling the liquid fraction from the flash zone to the reaction zone, and recovering acetic acid product from the flash zone vapour fraction by use of a single distillation zone by:
   (d) introducing the vapour fraction from the flash zone into the distillation zone, as a vapour and/or liquid.
   (e) removing from the head of the distillation zone a light ends recycle stream comprising water, methyl acetate, methyl iodide and acetic acid, and
   (f) removing from the distillation zone at a point below the introduction point of the flash zone vapour fraction, an acid product stream having a water concentration of less than 1500 ppm and a propionic acid concentration of less than 500 ppm.

2. A process as claimed in claim 1 in which the liquid reaction composition comprises a finite amount of water at a concentration of up to about 8% by weight, and the flash zone vapour fraction comprises water up to about 6% by weight.

3. A process as claimed in claim 1 in which the liquid reaction composition comprises an iodide salt which suppresses the volatility of water relative to that of acetic acid.

4. A process as claimed in claim 3 in which the iodide salt which suppresses the volatility of water relative to that of acetic acid comprises at least one salt selected from the group consisting of iodide salts of alkali and alkaline earth metals and hydrogen and aluminium.

5. A process as claimed in claim 1 in which the methyl acetate concentration in the liquid reaction composition is in the range 2 to 15% by weight.

6. A process as claimed in claim 1 in which the concentration of corrosion metals which have an adverse effect on the carbonylation reaction is less than 1000 ppm in the liquid reaction composition.

7. A process as claimed in claim 6 in which said corrosion metals comprise at least one metal selected from the group consisting of iron, manganese and nickel.

8. A process as claimed in claim 1 in which the single distillation zone has up to 25 theoretical stages.

9. A process as claimed in claim 1 in which the single distillation zone has about 4 to 15 theoretical rectifying stages above the feed point.

10. A process as claimed in claim 1 in which the single distillation zone has up to about 14 theoretical stripping stages below the feedpoint.

11. A process as claimed in claim 1 in which the single distillation zone has up to 50 actual separation stages.

12. A process as claimed in claim 1 in which the acetic acid product is passed through one or more ion exchange resin beds to remove iodide contaminants.

13. A process as claimed in claim 12 in which the one or more ion exchange resins comprises an anion exchange resin.

14. A process as claimed in claim 12 in which the one or more ion exchange resins comprises a silver-loaded resin.

15. A process as claimed in claim 1 in which the liquid reaction composition comprises:
   (a) up to about 8% by weight water and, (b) 2 to 15% by weight methyl acetate, and in which the flash zone vapour fraction comprises up to about 6% by weight water and in which the single distillation zone has up to 25 theoretical stages.

16. A process as claimed in claim 15 in which the liquid reaction composition comprises an iodide salt which suppresses the volatility of water relative to that of acetic acid.

17. A process as claimed in claim 16 in which the iodide salt which suppresses the volatility of water relative to that of acetic acid comprises at least one salt selected from the group consisting of iodide salts of alkali and alkaline earth metals and hydrogen and aluminium.

18. A process as claimed in claim 17 in which the single distillation zone has about 4 to 15 theoretical rectifying stages above the feed point.

19. A process as claimed in claim 18 in which the single distillation zone has up to about 14 theoretical stripping stages below the feedpoint.

20. A process as claimed in claim 19 in which the single distillation zone has up to 50 actual separation stages.

21. A process as claimed in claim 20 in which the acetic acid product is passed through one or more ion exchange resin beds to remove iodide contaminants.

22. A process as claimed in claim 21 in which the one or more ion exchange resins comprises an anion exchange resin.

23. A process as claimed in claim 21 in which the one or more ion exchange resins comprises a silver-loaded resin.

24. A process as claimed in claim 15, 16, 17, 18, 19 or 20 in which the liquid reaction composition contains less than 1000 ppm of corrosion metals which have an adverse effect on the carbonylation reaction.

25. A process as claimed in claim 15, 16, 17, 18, 19, or 20, in which the acetic acid product is passed through one or more ion exchange resin beds to remove iodide contaminants.

26. A process as claimed in claim 25 in which the one or more ion exchange resins comprises an anion exchange resin.

27. A process as claimed in claim 25 in which the one or more ion exchange resins comprises a silver-loaded resin.

* * * * *

UNITED STATES PATENT AND TRADEMARK OFFICE
CERTIFICATE OF CORRECTION

PATENT NO.   : 5,416,237
DATED        : May 16, 1995
INVENTOR(S)  : SIMON D. AUBIGNE, JEREMY B. COOPER, BRUCE L. WILLIAMS and DERRICK J. WATSON It is certified that error appears in the above-indentified patent and that said Letters Patent is hereby corrected as shown below:

Col. 7, l. 13, change "bare" to --barg--

Col. 7, l. 14, change "bare" to --barg--

Col. 12, l. 13, there should be a comma (,) not a period (.) after "liquid"

Col. 12, line 68, claim 15, line 3, "water and, " should read --water, and--.
Col. 14, line 15,
 Claim 25, line 2, delete the comma (,) after "20"

Signed and Sealed this

Nineteenth Day of September, 1995

Attest:

BRUCE LEHMAN

Attesting Officer        Commissioner of Patents and Trademarks